United States Patent [19]
Tomley et al.

[11] Patent Number: 6,001,363
[45] Date of Patent: Dec. 14, 1999

[54] COCCIDIOSIS POULTRY VACCINE

[75] Inventors: Fiona Margaret Tomley, Oxford; Paul Patric James Dunn, Oxfordshire; Janene Marylin Bumstead, Wantage, all of United Kingdom; Arnoldus Nicolaas Vermeulen, Cuyk, Netherlands

[73] Assignee: Akzo Nobel, N.V., Arnhem, Netherlands

[21] Appl. No.: 09/013,780

[22] Filed: Jan. 26, 1998

Related U.S. Application Data

[62] Division of application No. 08/527,044, Sep. 12, 1995, Pat. No. 5,885,568.

[30] Foreign Application Priority Data

Sep. 16, 1994 [EP] European Pat. Off. .............. 94202676

[51] Int. Cl.⁶ ..................... A61K 39/00; A61K 39/012; C07K 1/00
[52] U.S. Cl. ..................... 424/191.1; 424/267.1; 530/350
[58] Field of Search ................. 530/350; 424/191.1, 424/267.1

[56] References Cited

U.S. PATENT DOCUMENTS 5,496,550  3/1996  Wallach et al. .

FOREIGN PATENT DOCUMENTS

| | | |
|---|---|---|
| 0223710 | 5/1987 | European Pat. Off. . |
| 0328253 | 8/1989 | European Pat. Off. . |
| 0653489 | 5/1995 | European Pat. Off. . |
| WO A 9204460 | 3/1992 | WIPO . |
| WO A 9216627 | 10/1992 | WIPO . |

OTHER PUBLICATIONS

C. Ko et al., *Molecular and Biochemical Parasitology*, 41:53–64, 1990.

A. Rhalem et al., *Veterinary Immunology and Immunopathology*, 38:3–4:327–340, Oct., 1993.

Fried et al., *Molecular and Biochemical Parasitology*, 51:251–262, 1992.

*Primary Examiner*—Anthony C. Caputa
*Assistant Examiner*—Mark Navarro
*Attorney, Agent, or Firm*—Mary E. Gormley

[57] ABSTRACT

This invention relates to a novel Eimeria protein with immunogenic properties as well as to DNA sequences encoding these proteins. This protein can be administered to poultry thereby protecting the birds against coccidiosis. In addition the DNA encoding this protein can be used for the preparation of a vector vaccine against coccidiosis.

6 Claims, 5 Drawing Sheets

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 392 base pairs
      (B) TYPE: nucleic acid
      (C) STRANDEDNESS: double
      (D) TOPOLOGY: linear

```
    (ii) MOLECULE TYPE: cDNA to mRNA (iii) HYPOTHETICAL: NO (iii) ANTI-SENSE: NO (vi) ORIGINAL SOURCE:
         (A) ORGANISM: Eimeria maxima
         (B) STRAIN: Houghton
         (D) DEVELOPMENTAL STAGE: Sporozoite (vii) IMMEDIATE SOURCE:
         (A) LIBRARY: sporozoite cDNA cloned in Lambda ZAPII
         (B) CLONE: Em45-9

(ix) FEATURE:
         (A) NAME/KEY: CDS
         (B) LOCATION: 3..329

(xi) SEQUENCE DESCRIPTION: SEQ ID NO: 1:

CA ACA GCA GAT GCT TAT TTA ACA AAC GCC TGC TGC TGT CTT AGA TAC        47
   Thr Ala Asp Ala Tyr Leu Thr Asn Ala Cys Cys Cys Leu Arg Tyr
   1               5                  10                  15

ACG AAC TCT TGC TGC AGC AAG TAT TGC TGC AGC AAG TGT TGC TGC AGC        95
Thr Asn Ser Cys Cys Ser Lys Tyr Cys Cys Ser Lys Cys Cys Cys Ser
            20                  25                  30

AAG TGT TGC TGC AGC AAA TGC TGC TGC AGC ACG TAT TGC TGC AGT ACG       143
Lys Cys Cys Cys Ser Lys Cys Cys Cys Ser Thr Tyr Cys Cys Ser Thr
                35                  40                  45

TTC TGC TGC AGC AAG TGC TGC TGC AGC AAG TTT TGC TGC AAT AGA TTT       191
Phe Cys Cys Ser Lys Cys Cys Cys Ser Lys Phe Cys Cys Asn Arg Phe
            50                  55                  60

AGT AAT AGA TTT TGC TGC AGC AGA ATG CTG CTG CAG CAA CTT TTG CTG       239
Ser Asn Arg Phe Cys Cys Ser Arg Met Leu Leu Gln Gln Leu Leu Leu
65                  70                  75

CAG CAA GGT TTG CTG CAA CAA GCT TTT GCT GCA GCA TTT GCT GCT GCA       287
Gln Gln Gly Leu Leu Gln Gln Ala Phe Ala Ala Ala Phe Ala Ala Ala
80                  85                  90                  95

GCA GGT GCT GCT GCA GCA AGT GCT GCT GCA GCA TGC ACA GAC                329
Ala Gly Ala Ala Ala Ala Ser Ala Ala Ala Ala Cys Thr Asp
                100                 105

TAGCCTGTAT TACACAGGGA GCCTTAACCT TTCCGCCTGT TGTTAAAAAA AAAAAAAAAA     389

AAA                                                                    392

(2) INFORMATION FOR SEQ ID NO: 2:

(i) SEQUENCE CHARACTERISTICS:
         (A) LENGTH: 109 amino acids
         (B) TYPE: amino acid
         (D) TOPOLOGY: linear (ii) MOLECULE TYPE: protein (xi) SEQUENCE DESCRIPTION: SEQ ID NO: 2:

Thr Ala Asp Ala Tyr Leu Thr Asn Ala Cys Cys Cys Leu Arg Tyr Thr
1               5                  10                  15

Asn Ser Cys Cys Ser Lys Tyr Cys Cys Ser Lys Cys Cys Ser Lys
            20                  25                  30

Cys Cys Cys Ser Lys Cys Cys Cys Ser Thr Tyr Cys Cys Ser Thr Phe
                35                  40                  45

Cys Cys Ser Lys Cys Cys Cys Ser Lys Phe Cys Cys Asn Arg Phe Ser
            50                  55                  60

Asn Arg Phe Cys Cys Ser Arg Met Leu Leu Gln Gln Leu Leu Leu Gln
65                  70                  75                  80
```

```
Gln Gly Leu Leu Gln Gln Ala Phe Ala Ala Ala Phe Ala Ala Ala
                85                  90                  95

Gly Ala Ala Ala Ala Ser Ala Ala Ala Cys Thr Asp
            100                 105
```

COCCIDIOSIS POULTRY VACCINE

This is a division of application Ser. No. 08/527,044 filed Sep. 12, 1995, now U.S. Pat. No. 5,885,568, which is hereby incorporated by reference.

The present invention relates to a protein derived from an Eimerian species, in particular *Eimeria maxima*, which is capable of stimulating immune lymphocytes. It also relates to a nucleic acid sequence encoding all or an antigenically significant part of this protein, a recombinant vector comprising such a nucleic acid sequence, a host cell or organism transformed with such a recombinant vector and a vaccine for the protection of poultry against coccidiosis.

Coccidiosis is a disease caused by infection with one or more of the many species of coccidia, intracellular protozoal parasites of the subphylum Apicomplexa and the genus Eimeria. Poultry is defined herein as domesticated birds that serve as a source of eggs or meat and that include such commercially important kinds as chickens, turkeys, ducks, geese, guinea fowl, pheasants, pigeons and peafowl.

Coccidiosis in chickens is known to be caused by several different species of Eimeria, namely *Eimeria acervulina, E. maxima, E. tenella, E. necatrix, E. brunetti, E. mitis, E. praecox, E. mivati* and *E. hagani*. Some people, however, doubt the true existence of the last two species. Low level infection with any of these Eimeria species results in a protective immunity to reinfection.

The species do differ in their pathogenic effect on chickens, the type of chicken also playing a role; thus, a broiler chicken will be subjected to a great deal of damage by a parasite such as *E. acervulina* or *E. maxima* because these parasitise large portions of the small intestine, where food digestion plays a major role.

*E. maxima* is the most immunogenic of the species listed above, producing good natural protection following infection. There are, however, strain variations with little or no cross protection between strains.

During the life cycle, the Eimeria parasite passes through a number of stages. The life cycle begins when the chicken ingests the infectious stage, known as the sporulating oocyst, during ground feeding or by inhalation of dust. In the case of *E. maxima*, the oocyst is unusually large. The wall of the sporulated oocyst is ruptured by a combination of mechanical grinding action and chemical action in the gizzard and intestinal tract, resulting in the release of four sporocysts. The sporocysts pass into the duodenum where they are exposed to bile and digestive enzymes resulting in the release of an average of two sporozoites per sporocyst.

The sporozoites are mobile and search for suitable host epithelium cells in order to penetrate and reproduce in them. Following infection of an epithelium cell, the parasite enters the schizont phase of its life cycle, producing from 8 to 16 to >200 merozoites per schizont. Once released from the schizont, the merozoites are free to infect further epithelium cells. After from two to five of these asexual reproduction cycles, the intracellular merozoites grow into sexual forms known as the female or macrogametocyte and the male or microgametocyte. Following fertilization of the macrogametocyte by the microgametes released from the microgametocyte, a zygote is formed which creates a cyst wall about itself. The newly formed oocyst is passed out of the infected chicken with the droppings.

With the correct environmental conditions of temperature and humidity and sufficient oxygen in the air, the oocyst will sporulate into the infectious stage, ready to infect a new host and thereby spreading the disease. Thus no intermediate host is required for transfer of the parasite from bird to bird.

The result of the Eimeria parasite infecting the digestive tract of a chicken may be a reduction in weight gain, decreased feed conversion, cessation of egg production and, in some cases, death. The increase in intensive production of poultry has been accompanied by severe losses due to this parasite; indeed, coccidiosis has become the most economically important parasitic disease. In the Netherlands, the losses that poultry farmers suffer every year run into millions of guilders; in 1986 the loss was about 13 million guilders. In the same year, a loss of 300 million dollars was suffered in the United States.

In the past, several methods have been used in attempts to control coccidiosis. Prior to the advent of chemotherapeutic agents, improved sanitation using disinfectants, together with the mechanical removal of litter, was the main method employed; sufficient oocysts, however, usually remained to transmit the disease.

The introduction of coccidiostatic agents in the feed or drinking water, in addition to good management, resulted in some success at disease control. Such agents have been found to suffer from a drop in effectiveness over the years, due partly to the development of drug resistant strains of coccidia. Furthermore, several chemotherapeutic agents have been found to leave residues in the meat, making it unsuitable for consumption.

Attempts have been made to control the disease immunologically by administering to chickens a live vaccine comprising oocysts from all seven species of Eimeria, the oocysts administered being from precocious lines. Such precocious lines are obtained by inoculating chickens with a wild population of an Eimeria species and collecting the very first parasites that are excreted as a result of the infection. The collected parasites are put back into chickens and the cycle repeated several times. Eventually a precocious line of parasite is produced which has fewer cycles of asexual reproduction in the gut. Thus such lines retain their immunogenicity, whilst producing fewer parasites in the gut with less consequential damage being caused to the host chicken. The disadvantage of this type of vaccine is that it is expensive to produce because of the necessity of producing it in live chickens and its lower reproductive potential.

The advent of genetic engineering has provided new methods for producing effective vaccines. Using these methods, the DNA coding for the antigenic proteins of some pathogenic microorganisms has been cloned into such host microorganisms as *Escherichia coli*, with the result that the protein has been expressed at sufficiently high levels such that it can be incorporated into a vaccine. The advantage of proteins produced in this way is that they are noninfectious and are relatively cheap to produce. In this way, vaccines have been prepared against a number of viruses such as hepatitis, herpes simplex and foot and mouth disease.

Attempts have been made to genetically engineer a coccidiosis vaccine. European patent application No. 337 589 describes the isolation of a Group B *Eimeria tenella* protein and its insertion into a novel expression vector which, in turn, has been used to transform appropriate hosts. Patent Cooperation Treaty Application WO 92/04461 describes the construction of a microorganism that produces an antigenic protein using either the "mRNA route" or the "nuclear DNA route". In this way, certain antigens from *E. tenella* and *E. maxima* were prepared and sequenced. Taking this type of route to prepare antigens for incorporation into a vaccine relies only upon selecting antigens which could induce antibodies in a heterologous species. This approach does not necessarily end up with selecting the most protective antigen.

It has now been found that by fractionating Eimeria parasites and selecting proteins that stimulate immune T-lymphocytes, then preparing vectors containing the nucleic acid coding for such proteins and subsequently preparing a vaccine containing such proteins, a more effectively protective coccidiosis vaccine may be produced.

According to one aspect of the invention, there is provided a nucleic acid sequence encoding all or a substantial part, in particular the immunologically active part, of a purified Eimeria T-lymphocyte stimulatory protein. Such a nucleic acid sequence may be operatively linked to expression control sequences resulting in a recombinant nucleic acid molecule which, when inserted into a suitable vector, results in a recombinant vector capable of expressing the nucleic acid sequence.

Such a recombinant vector, or nucleic acid sequence as defined above, may be used to transform a suitable host cell or organism. Such a transformed host cell or organism may, in turn, be used to produce the stimulatory protein for incorporation into a vaccine for the protection of poultry against coccidiosis. Alternatively, the transformed host cell or organism may itself be incorporated into a vaccine.

In general, the term "protein" refers to a molecular chain of amino acids with biological activity. A protein is not of a specific length and can, if required, be modified in vivo or in vitro, by, for example, glycosylation, amidation, carboxylation or phosphorylation; thus, inter alia, peptides, oligopeptides and polypeptides are included within the definition.

More particularly, this invention provides T-lymphocyte stimulatory proteins, or immunogenically active parts thereof, which comprise the amino acid sequence shown in SEQ ID NO. 2 and their biologically functional equivalents or variants.

The biologically functional equivalents or variants of the proteins specifically disclosed herein are proteins derived from the above noted amino acid sequences, for example by deletions, insertions and/or substitutions of one or more amino acids, but retain one or more immunogenic determinants of the Eimeria antigens, i.e. said variants have one or more epitopes capable of eliciting an immune response in a host animal.

It will be understood that, for the particular proteins embraced herein, natural variations can exist between individual Eimeria parasites or strains. These variations may be demonstrated by (an) amino acid differences) in the overall sequence or by deletions, substitutions, insertions, inversions or additions of (an) amino acid(s) in said sequence. Amino acid substitutions which do not essentially alter biological and immunological activities, have been described, e.g. by Neurath et al in "The Proteins" Academic Press New York (1979). Amino acid replacements between related amino acids or replacements which have occurred frequently in evolution are, inter alia, Ser/Ala, Ser/Gly, Asp/Gly, Asp/Asn, Ile/Val (see Dayhof, M.D., Atlas of protein sequence and structure, Nat. Biomed. Res. Found., Washington D.C., 1978, vol. 5, suppl. 3). Other amino acid substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, Lipman and Pearson developed a method for rapid and sensitive protein comparison (*Science,* 227, 1435–1441, 1985) and determining the functional similarity between homologous proteins. Such amino acid substitutions of the exemplary embodiments of this invention are within the scope of the invention as long as the resulting proteins retain their immunoreactivity.

The invention further provides isolated and purified nucleic acid sequences encoding the above mentioned proteins of Eimeria. Such a nucleic acid sequence is shown in SEQ. ID. NO: 1. It is well known in the art that the degeneracy of the genetic code permits substitution of bases in the codon resulting in another codon but still coding for the same amino acid, e.g. the codon for the amino acid glutamic acid is both GAT and GAA. Consequently, it is clear that, for the expression of a protein with the amino acid sequence shown in SEQ. ID. NO: 2, the nucleic acid sequence may have a codon composition different from the nucleic acid sequence shown in SEQ. ID. NO: 1.

*Eimeria maxima* parasites were produced by passage through chickens as described by Long et al (*Folio Vet. Lat.,* 1976, 6, 201–207). Oocysts were isolated from the faeces of the infected chickens, sporulated and then purified by floatation in saturated sodium chloride. The sporulated oocysts were then used to infect pathogen-free 4 week old chickens. A further dose of sporulated oocysts was administered to the birds in order to boost their immune response.

A preparation of sporulated oocysts purified by floatation as described above was subjected to vibration in a disintegrator in order to release sporozoites. The sporozoites were treated with proteolytic enzymes in order to release sporozoites which were then washed and purified by ion-exchange chromatography according to the method of Schmatz et al (*J. Protozool.,* 1984, 31, 181–183). The sporozoites were suspended in buffer, boiled in a water bath and spun prior to loading on a polyacrylamide gel for SDS-PAGE(sodium dodecyl sulphate polyacrylamide gel electrophoresis). Molecular mass markers were run on the same gel in order to extrapolate the molecular mass of the Eimeria antigens. The gel was electrophoresed onto nitrocellulose paper by the method of Towbin and Gordon,(*J.Immunol. Methods.,* 1984, 72, 313–340). The nitrocellulose paper was then washed and visualised by Aurodye staining according to the manufacturer's instructions.

Protein bands were excised from the nitrocellulose paper, cut into small pieces and transferred to glass vials, based on the method by Abou-Zeid et al. (J. Imm. Meth. 98, 5–10, 1987). The nitrocellulose pieces were then solubilised in dimethyl sulphoxide (DMSO) and left for a period of time to ensure solubilization, after which the nitrocellulose particles were precipitated by dropwise addition of carbonate/bicarbonate buffer with vigorous vortexing. Samples were then centrifuged, the pellets of nitrocellulose particles were washed several times after which they were resuspended and divided into small aliquots.

In order to determine whether any of the protein bands from the electrophoresis gel stimulated the lymphocytes from infected birds, blood was withdrawn by venapuncture from the chickens infected as described above, for use in a lymphocyte proliferation assay. The blood was centrifuged at 600 g, after 10 minutes the suspension of cells above the sedimented erythrocytes was removed and centrifuged at 400 g for a further 10 minutes. The cells deposited after the second centrifugation were washed several times and finally resuspended. The resuspended cells were cultured in round bottomed plates together with the diluted resuspended nitrocellulose particles. Control wells were set up containing nitrocellulose particles devoid of protein.

The lymphocyte cultures were incubated for 96 hours, during the last 16 hours of which the cultures were pulsed with $^{3}$H-thymidine, following which the cells were harvested onto glass microfibre filters. After drying, the filters were placed in scintillation vials to which was added liquid scintillation cocktail (Scintillator 299 [registered trade mark] Packard, Caversham, U.K.) and the radioactivity was measured in a scintillation spectrophotometer. The results were expressed as a stimulation index (SI) obtained using the following formula:

$$SI = cpm1/cpm2$$

where:

cpm1=average counts per minute of triplicate cultures incubated with NC particles bearing protein.

cpm2=average counts per minute of triplicate cultures incubated with NC particles devoid of protein.

By this method mostly T-lymphocytes are proliferating.

The results showed that although the stimulation index varied for different birds and different gels, a protein band, with a relative molecular mass (Mr) of approximately 45,000, gave consistant stimulation of lymphocytes from immunised but not control birds.

Following this discovery, a fresh preparation of *E. maxima* sporozoites was separated by SDS-PAGE and transferred to nitrocellulose as described above. A protein band with a Mr of 45,000 (p45) was excised, solubilised as described, washed in phosphate buffered saline (PBS) and then resuspended in PBS. This suspension was inoculated subcutaneously into rabbits, the injections being repeated every 2 weeks. Two weeks after each injection the rabbits were bled by venapuncture of a lateral ear vein. Rabbit anti-p45 serum was obtained after 5 boosts as determined by Western blotting.

Total ribonucleic acid (RNA) was extracted and purified from *E. maxima* sporozoites by centrifugation through a gradient of cesium trifluoroacetate. In order to separate the messenger RNA (mRNA) from non-mRNA, columns of oligo dT CELLULOSE (poly[A] Quik, Stratagene) were used according to the manufacturer's instructions. The poly (A)$^+$RNA or mRNA was then eluted from the column overnight using sodium acetate in absolute ethanol.

Copy deoxyribonucleic acid (cDNA) was synthesised from the mRNA using a ZAP-cDNA (registered trade mark) synthesis kit (Stratagene). The first strand of cDNA was synthesised using an oligo dT template (containing an XhoI restriction site) and Moloney-Murine Leukaemia Virus reverse transcriptase. The cytosine residues in the first strand of cDNA were methylated in order to protect the cDNA from digestion by restriction enzymes to be used later in the cloning protocol. The second strand of cDNA was synthesised using RNAse H and DNA polymerase I followed by end-repairing using T4 DNA polymerase. EcoRI adapters were ligated to the blunt ended cDNA by T4 DNA ligase. Digestion with XhoI produced cDNA with an XhoI compatible 3' end and an EcoRI compatible 5' end.

The cDNA was ligated to EcoRI/XhoI digested and dephosphorylated Uni-ZAP XR vector using T4 DNA ligase. The resulting primary libraries (Emx8 and Emx9) were plated and amplified on *E. coli* SURE cell. It was found that the Emx8 library gave 65% recombinants, whereas the Emx9 library gave 55% recombinants.

The two libraries, Emx8 and Emx9, were screened using rabbit anti-p45 serum, prepared as described above. Positive plaques were picked out, and re-screened until the positives were plaque pure.

The cDNA from clones in the two libraries, Emx8 and Emx9 were subcloned into plasmid pUC19 and analysed by digestion with restriction endonucleases. Alternatively, the cDNAs were subjected to plasmid rescue from lambda Zap using in vivo excision and subsequently analysed by digestion with restriction endonucleases.

In this way several different clones were identified. Selected antisera for two of the clones crossreacted with different spots recognised by the anti-p45 antisera on blots of *E. maxima* sporozoites separated by 2d PAGE, these clones were then selected for DNA sequence analysis. This was carried out by random subcloning and sequencing using the M13/dideoxynucleotide chain termination method described by Bankier et al. (Techniques in the Life Sciences (Biochemistry) 85: techniques in Nucleic Acids Biochemstry 1–34, 1983).

A nucleic acid sequence according to the present invention may be isolated from a particular Eimeria strain and multiplied by recombinant DNA techniques including polymerase chain reaction (PCR) technology or may be chemically synthesized in vitro by techniques known in the art.

A nucleic acid sequence according to the invention can be ligated to various replication effecting DNA sequences with which it is not associated, or linked in nature, resulting in a so-called recombinant vector which can be used for the transformation of a suitable host. Useful recombinant vectors are preferably derived from plasmids, bacteriophages, cosmids or viruses.

Specific vectors or cloning vehicles which can be used to clone nucleic acid sequences according to the invention are known in the art and include inter alia plasmid vectors such as pBR322, the various pUC, pGEM and Bluescript plasmids; bacteriophages, e.g. lambdagt-Wes, Charon 28 and the M13 derived phages or viral vectors such as SV40, adenovirus or polyoma virus (see also Rodriquez, R. L. and D. T. Denhardt, ed., Vectors: A survey of molecular cloning vectors and their uses, Butterworths, 1988; Lenstra, J. A. et al., *Arch. Virol.*, 110, 1–24, 1990). The methods to be used for the construction of a recombinant vector according to the invention are known to those of ordinary skill in the art and are inter alia set forth in Maniatis, T. et al. (Molecular Cloning A Laboratory Manual, second edition; Cold Spring Harbor Laboratory, 1989).

For example, the insertion of the nucleic acid sequence according to the invention into a cloning vector can easily be achieved when both the genes and the desired cloning vehicle have been cut with the same restriction enzyme(s) as complementary DNA termini are thereby produced.

Alternatively, it may be necessary to modify the restriction sites that are produced into blunt ends either by digesting the single-stranded DNA or by filling in the single-stranded termini with an appropriate DNA polymerase. Subsequently, blunt end ligation with an enzyme such as T4 DNA ligase may be carried out.

If desired, any restriction site may be produced by ligating linkers onto the DNA termini. Such linkers may comprise specific oligonucleotide sequences that encode restriction site sequences. The restriction enzyme cleaved vector and nucleic acid sequence may also be modified by homopolymeric tailing.

"Transformation", as used herein, refers to the introduction of an heterologous nucleic acid sequence into a host cell, irrespective of the method used, for example direct uptake or transduction. The heterologous nucleic acid sequence may be maintained through autonomous replication or, alternatively, may be integrated into the host genome. If desired, the recombinant vectors are provided with appropriate control sequences compatible with the designated host. These sequences can regulate the expression of the inserted nucleic acid sequence. In addition to microorganisms, cell cultures derived from multicellular organisms may also be used as hosts.

The recombinant vectors according to the invention preferably contain one or more marker activities that Lay be used to select for desired transformants, such as ampicillin and tetracycline resistance in pBR322, ampicillin resistance and α-peptide of β-galactosidase in pUC8.

A suitable host cell is a microorganism or cell which can be transformed by a nucleic acid sequence encoding a polypeptide or by a recombinant vector comprising such a nucleic acid sequence, and which can, if desired, be used to express said polypeptide encoded by said nucleic acid sequence. The host cell can be of prokaryotic origin, e.g. bacteria such as *Escherichia coli, Bacillus subtilis* and *Pseudomonas* species; or of eukaryotic origin such as yeasts, e.g. *Saccharomyces cerevisiae* or higher eukaryotic cells such as insect, plant or mammalian cells, including HeLa cells and Chinese hamster ovary (CHO) cells. Insect cells include the Sf9 cell line of *Spodoptera frugiperda* (Luckow et al., *Biotechnology* 6, 47–55, 1988). Information with respect to the cloning and expression of the nucleic acid sequence of the present invention in eukaryotic cloning systems can be found in Esser, K. et al. (Plasmids of Eukaryotes, Springer-Verlag, 1986).

In general, prokaryotes are preferred for the construction of the recombinant vectors useful in the present invention. *E. coli* K12 strains are particularly useful, especially DH5a or MC1061 strains.

For expression, nucleic acid sequences of the present invention are introduced into an expression vector, i.e. said sequences are operably linked to expression control sequences. Such control sequences may comprise promoters, enhancers, operators, inducers, ribosome binding sites etc. Therefore, the present invention provides a recombinant vector comprising a nucleic acid sequence encoding an Eimeria protein identified above operably linked to expression control sequences, which is capable of expressing the DNA sequences contained therein in (a) transformed host cell(s).

It should be understood, of course, that the nucleotide sequences inserted at the selected site of the cloning vector may include nucleotides which are not part of the actual structural gene for the desired polypeptide, or may include only a fragment of the complete structural gene for the desired protein as long as the transformed host will produce a polypeptide having at least one or more immunogenic determinants of an Eimeria protein antigen.

When the host cells are bacteria, useful expression control sequences which may be used include the Trp promotor and operator (Goeddel, et al., *Nucl. Acids Res.,* 8, 4057, 1980); the lac promotor and operator (Chang, et al., *Nature,* 275, 615, 1978); the outer membrane protein promotor (Nakamura, K. and Inouge, M., *EMBO J.,* 1, 771–775, 1982); the bacteriophage lambda promotors and operators (Remaut, E. et al., *Nucl. Acids Res.,* 11, 4677–4688, 1983); the α-amylase (*B. subtilis*) promotor and operator, termination sequences and other expression enhancement and control sequences compatible with the selected host cell. When the host cell is yeast, illustrative useful expression control sequences include, e.g., α-mating factor. For insect cells the polyhedrin or p10 promotors of baculoviruses can be used (Smith, G. E. et al., *Mol. Cell. Biol.* 3, 2156–65, 1983). When the host cell is of mammalian origin illustrative useful expression control sequences include the SV-40 promotor (Berman, P. W. et al., *Science,* 222, 524–527, 1983) or the metallothionein promotor (Brinster, R. L., *Nature,* 296, 39–42, 1982) or a heat shock promotor (Voellmy et al., *Proc. Natl. Acad. Sci. USA,* 82, 4949–53, 1985). Alternatively, expression control sequences present in Eimeria may also be applied. For maximizing gene expression, see also Roberts and Lauer (*Methods in Enzymology,* 68, 473, 1979).

Therefore, the invention also comprises (a) host cell(s) containing a nucleic acid sequence or a recombinant nucleic acid molecule or a recombinant vector described above, capable of producing the Eimeria protein by expression of the nucleic acid sequence.

Immunization of poultry against Eimeria infection can be achieved by administering to the birds a protein according to the invention in an immunologically relevant context as a so-called subunit vaccine. The subunit vaccine according to the invention may comprise a protein in a pure form, optionally in the presence of a pharmaceutically acceptable carrier. The protein can optionally be covalently bonded to a non-related protein, which can be of advantage in the purification of the fusion product. Examples are β-galactosidase, protein A, prochymosine, blood clotting factor Xa, etc.

In some cases the ability to raise protective immunity using these proteins per se may be low. Small fragments are preferably conjugated to carrier molecules in order to raise their immunogenicity. Suitable carriers for this purpose are macromolecules, such as natural polymers (proteins like key hole limpet hemocyanin, albumin, toxins), synthetic polymers like polyamino acids (polylysine, polyalanine), or micelles of amphiphilic compounds like saponins. Alternatively these fragments may be provided as polymers thereof, preferably linear polymers.

If required, the proteins according to the invention which are to be used in a vaccine can be modified in vitro or in vivo, for example by glycosylation, amidation, carboxylation or phosphorylation.

An alternative to subunit vaccines is live vaccines. A nucleic acid sequence according to the invention is introduced by recombinant DNA techniques into a microorganism (e.g. a bacterium or virus) in such a way that the recombinant microorganism is still able to replicate, thereby expressing a polypeptide coded by the inserted nucleic acid sequence and eliciting an immune response in the infected host bird.

A preferred embodiment of the present invention is a recombinant vector virus comprising an heterologous nucleic acid sequence described above, capable of expressing the DNA sequence in (a) host cell(s) or host bird infected with the recombinant vector virus. The term "heterologous" indicates that the nucleic acid sequence according to the invention is not normally present in nature in the vector virus.

Furthermore, the invention also comprises (a) host cell(s) or cell culture infected with the recombinant vector virus, capable of producing the Eimeria protein by expression of the nucleic acid sequence.

For example the well known technique of in vivo homologous recombination can be used to introduce an heterologous nucleic acid sequence according to the invention into the genome of the vector virus.

First, a DNA fragment corresponding with an insertion region of the vector genome, i.e. a region which can be used for the incorporation of an heterologous sequence without disrupting essential functions of the vector such as those necessary for infection or replication, is inserted into a cloning vector according to standard recDNA techniques. Insertion-regions have been reported for a large number of microorganisms (e.g. EP 80,806, EP 110,385, EP 83,286, EP 314,569, WO 88/02022, WO 88/07088, U.S. Pat. No. 4,769, 330 and U.S. Pat. No. 4,722,848).

Second, if desired, a deletion can be introduced into the insertion region present in the recombinant vector molecule obtained from the first step. This can be achieved for example by appropriate exonuclease III digestion or restriction enzyme treatment of the recombinant vector molecule from the first step.

Third, the heterologous nucleic acid sequence is inserted into the insertion-region present in the recombinant vector of the first step or in place of the DNA deleted from said recombinant vector. The insertion region DNA sequence should be of appropriate length as to allow homologous recombination with the vector genome to occur. Thereafter, suitable cells can be infected with wild-type vector virus or transformed with vector genomic DNA in the presence of the recombinant vector containing the insertion flanked by appropriate vector DNA sequences whereby recombination occurs between the corresponding regions in the recombinant vector and the vector genome. Recombinant vector progeny can now be produced in cell culture and can be selected for example genotypically or phenotypically, e.g. by hybridization, detecting enzyme activity encoded by a gene co-integrated along with the heterologous nucleic acid sequence, or detecting the antigenic heterologous polypeptide expressed by the recombinant vector immunologically.

Next, this recombinant microorganisms can be administered to poultry for immunization whereafter it maintains itself for some time, or even replicates in the body of the inoculated animal, expressing in vivo a polypeptide coded for by the inserted nucleic acid sequence according to the invention resulting in the stimulation of the immune system of the inoculated animal. Suitable vectors for the incorporation of a nucleic acid sequence according to the invention can be derived from viruses such as pox viruses, e.g. vaccinia virus (EP 110,385, EP 83,286, U.S. Pat. No. 4,769, 330 and U.S. Pat. No. 4,722 848) or fowl pox virus (WO 88/02022), herpes viruses such as HVT (WO 88/07088) or Marek's Disease virus, adeno virus or influenza virus, or bacteria such as *E. coli* or specific Salmonella species. With recombinant microorganisms of this type, the polypeptide synthesized in the host animal can be exposed as a surface antigen. In this context fusion of the polypeptide with OMP proteins, or pilus proteins of for example *E. coli* or synthetic provision of signal and anchor sequences which are recognized by the organism are conceivable. It is also possible that the Eimeria polypeptide, if desired as part of a larger whole, is released inside the animal to be immunized. In all of these cases it is also possible that one or more immunogenic products will find expression which generate protection against various pathogens and/or against various antigens of a given pathogen.

A vector vaccine according to the invention can be prepared by culturing a recombinant bacterium or a host cell infected with a recombinant vector comprising a nucleic acid sequence according to the invention, whereafter recombinant bacteria or vector confining cells and/or recombinant vector viruses grown in the cells can be collected, optionally in a pure form, and formed into a vaccine optionally in a lyophilised form.

A vector vaccine can also be prepared by transfecting other protozoan parasites such as Toxoplasma, Eimeria spp. or Leishmaniawith the DNA described in this invention.

But also naked DNA can be used as vaccine provided it is presented in a plasmid or in combination with suitable eukaryotic promoter sequences such as those from SV40 virus.

Host cells transformed with a recombinant vector according to the invention can also be cultured under conditions which are favourable for the expression of a polypeptide coded by said nucleic acid sequence. Vaccines may be prepared using samples of the crude culture, host cell lysates or host cell extracts, although in another embodiment more purified polypeptides according to the invention are formed into a vaccine, depending on its intended use. In order to purify the polypeptides produced, host cells transformed with a recombinant vector according to the invention are cultured in an adequate volume and the polypeptides produced are isolated from such cells, or from the medium if the protein is excreted. Polypeptides excreted into the medium can be isolated and purified by standard techniques, e.g. salt fractionation, centrifugation, ultrafiltration, chromatography, gel filtration or immuno affinity chromatography, whereas intracellular polypeptides can be isolated by first collecting said cells, disrupting the cells, for example by sonication or by other mechanically disruptive means such as French press, followed by separation of the polypeptides from the other intracellular components and forming the polypeptides into a vaccine. Cell disruption could also be achieved by chemical (e.g. EDTA or detergents such as Triton X114) or enzymatic means, such as lysozyme digestion.

Antibodies or antiserum directed against a polypeptide according to the invention have a potential use in passive immunotherapy, diagnostic immunoassays and generation of anti-idiotypic antibodies.

The Eimeria proteins as characterized above can be used to produce antibodies, both polyclonal, monospecific and monoclonal. If polyclonal antibodies are desired, techniques for producing and processing polyclonal sera are known in the art (e.g. Mayer and Walter. eds, Immunochemical Methods in Cell and Molecular Biology, Academic Press, London, 1987). Monospecific antibodies to an immunogen can be affinity purified from polyspecific antisera by a modification of the method of Hall et al. (*Nature*, 311, 379–387, 1984). Monospecific antibody, as used herein, is defined as a single antibody species or multiple antibody species with homogeneous binding characteristics for the relevant antigen. Homogeneous binding, as used herein, refers to the ability of the antibody species to bind to a specific antigen or epitope.

Monoclonal antibodies, reactive against the Eimeria proteins according to the present invention, can be prepared by immunizing inbred mice by techniques known in the art (Kohler and Milstein, *Nature*, 256, 495–497, 1975). Hybridoma cells are selected by growth in hypoxanthine, thymidine and aminopterin in an appropriate cell culture medium such as Dulbecco's modified Eagle's medium. Antibody producing hybridomas are cloned, preferably using the soft agar technique of MacPherson, (Soft Agar Techniques, Tissue Culture Methods and Applications, Kruse and Paterson, eds., Academic Press, 276, 1973). Discrete colonies are transferred into individual wells of culture plates for cultivation in an appropriate culture medium. Antibody producing cells are identified by screening with the appropriate immunogen. Immunogen positive hybridoma cells are maintained by techniques known in the art. Specific anti-monoclonal antibodies are produced by cultivating the hybridomas in vitro or preparing ascites fluid in mice following hybridoma injection by procedures known in the art.

Anti-idiotypic antibodies are immunoglobulins which carry an "internal image" of the antigen of the pathogen against which protection is desired and can be used as an immunogen in a vaccine (Dreesman et al., *J. Infect. Disease*, 151, 761, 1985). Techniques for raising anti-idiotypic antibodies are known in the art (MacNamara et al., *Science*, 226, 1325, 1984).

The vaccine according to the invention can be administered in a conventional active immunization scheme: single or repeated administration in a manner compatible with the dosage formulation, and in such amount as will be prophylactically effective, i.e. the amount of immunizing antigen or recombinant microorganism capable of expressing said antigen that will induce immunity in poultry against challenge by virulent Eimeria parasites. Immunity is defined as the induction of a significant level of protection in a population of chickens after vaccination compared to an unvaccinated group.

For live viral vector vaccines the dose rate per chicken may range from $10^5$–$10^8$ pfu. A typical subunit vaccine according to the invention comprises 1 µg–1 mg of the protein according to the invention. Such vaccines can be administered intradermally, subcutaneously, intramuscularly, intraperitoneally, intravenously, orally or intranasally.

Additionally the vaccine may also contain an aqueous medium or a water containing suspension, often mixed with other constituents in order to increase the activity and/or the shelf life. These constituents may be salts, pH buffers, stabilizers (such as skimmed milk or casein hydrolysate), emulsifiers, adjuvants to improve the immune response (e.g. oils, muramyl dipeptide, aluminium hydroxide, saponin, polyanions and amphipatic substances) and preservatives.

It is clear that a vaccine according to the invention may also contain immunogens related to other pathogens of poultry, or may contain nucleic acid sequences encoding these immunogens, like antigens of Marek's Disease virus (MDV), Newcastle Disease virus (NDV), Infectious Bronchitis virus (IBV), Chicken Anemia Agent (CAA), Reo virus, Avian Retro virus, Fowl Adeno virus, Turkey Rhinotracheitis virus, E. coli or other Eimeria species to produce a multivalent vaccine.

The invention also relates to an "immunochemical reagent", which reagent comprises a protein according to the invention. The term "immunochemical reagent" signifies that the protein according to the invention is bound to a suitable support or is provided with a labelling substance.

The supports that may be used are, for example, the inner wall of a microtest well or a cuvette, a tube or capillary, a membrane, filter, test strip or the surface of a particle such as, for example, a latex particle, an erythrocyte, a dye sol, a metal sol or metal compound as sol particle.

Labelling substances which can be used are, inter alia, a radioactive isotope, a fluorescent compound, an enzyme, a dye sol, metal sol or metal compound as sol particle.

A nucleic acid sequence according to the invention can also be used to design specific probes for hybridization experiments for the detection of Eimeria related nucleic acids in any kind of tissue.

The present invention also comprises a test kit comprising said nucleic acid sequence useful for the diagnosis of Eimeria infection.

The invention also relates to a test kit to be used in an immunoassay, this test kit containing at least one immunochemical reagent according to the invention. The immunochemical reaction which takes place using this test kit is preferably a sandwich reaction, an agglutination reaction, a competition reaction or an inhibition reaction.

For carrying out a sandwich reaction, the test kit can consist, for example, of a polypeptide according to the invention bonded to a solid support, for example the inner wall of a microtest well, and either a labelled polypeptide according to the invention or a labelled anti-antibody.

The invention is illustrated by the following examples.

EXAMPLE 1

Preparation of Antigens of E. maxima Sporozoites 1.a.i. Preparation of parasites Eimeria maxima Houghton strain (E. maxima H) parasites were passaged through Light Sussex chickens as described by Long et al. (Folio Vet. Lat., 1976, 6: 201–207). Oocysts were isolated from faeces, sporulated in 2% potassium dichromate at 29° C. for 72 hours, surface sterilised by washing in 10% sodium hypochlorite and purified by flotation in saturated sodium chloride. Sporulated oocysts were suspended in phosphate buffered saline (PBS) pH 7.6 and broken by vibration. Sporocysts were suspended in PBS pH 7.6 containing 0.5% w/v porcine bile (Difco) and 0.25% w/v trypsin (Difco 1:250) and incubated at 41° C. for 30 minutes. Released sporozoites were washed in PBS pH 8.0, purified on columns of DE-52 (Whatman) as described by Schmatz et al. (J. Protozool., 1984, 31: 181–183) and stored as pellets in eppendorf tubes at −70° C.

1.a.ii. Preparation of antigens

Sporozoite pellets (5×107) were solubilised by boiling for 10 minutes in 100 ml of sample buffer (5 mM Tris-Cl pH 6.8, 2% SDS, 10% glycerol, 100 mM DTT and 10 mg/ml bromophenol blue) then loaded onto a discontinuous SDS-polyacrylamide gel. Gels were electrophoresed and polypeptides were transferred to nitrocellulose (NC) paper by the method of Towbin and Gordon (J. Immunol. Methods, 1984, 72: 313–340). After transfer, the NC paper was rinsed in PBS pH 7.6 containing 0.3% Tween-20 and polypeptides were visualised by staining with colloidal gold (Aurodye, Cambio, England) according to the manufacturer's instructions.

The NC paper was cut into strips, each of which carried Eimeria polypeptides of a limited range of molecular mass. Each strip was cut into small pieces and the pieces transferred to labelled glass vials. To each vial, 400 ml of DMSO was added and the mixture left for 60 minutes to ensure solubilisation and sterilisation. NC particles were precipitated by the dropwise addition, with vigorous vortexing, of an equal volume of carbonate/bicarbonate buffer (5 mM, pH 9.6). Samples were transferred to 1.5 ml microcentrifuge tubes and centrifuged at 10,000 g for 5 minutes. NC particles were washed three times in RPMI 1640 medium (Gibco Biocult, Paisley, Scotland)), then finally suspended in 1 ml of this medium, divided into 200 ml aliquots, and stored frozen at −70° C.

EXAMPLE 2

Identification of Lymphostimulatory Antigens 2.a. Methods 2.a.i. Immunisation of animals For primary infections, groups of Reaseheath-C chickens (4 weeks old, 10 birds per group) were orally dosed with 4000 sporulated oocysts of E. maxima H. For secondary infections, the same birds were orally dosed with 50,000 sporulated oocysts of E. maxima H. For each experiment an age-matched control group of Reaseheath-C chickens were housed separately.

2.a.ii. Preparation of peripheral blood lymphocytes

Blood samples (5 ml) were withdrawn from superficial wing veins into plastic syringes containing heparin (10 units/ml). The blood was transferred to tubes (Falcon 2027, Becton-Dickinson) and centrifuged at 400 rpm for 15 minutes in a Sorvall RC3B centrifuge. The layer of cells above the sedimented erythrocytes was carefully removed by pipette into fresh tubes (Falcon 2059, Becton-Dickinson) and centrifuged at 2000 rpm for 10 minutes. The deposited cells were washed three times in RPMI 1640 containing 10% foetal calf serum (FCS, virus and mycoplasma screened, Gibco Biocult), 200 units/ml of penicillin and 200 mg/ml of streptomycin (G. R. Squibb & Sons, Moreton, England) and resuspended in the same medium at $4 \times 10^6$ cells/ml. 100 ml aliquots of cells ($4 \times 10^5$) were pipetted into round bottomed wells of 96-well plates (Nunc-Gibco, Paisley, Scotland). To each well, 100 µl of a prepared sample was added. Test samples consisted of prepared NC particle suspensions (see Example 1a.i) diluted in RPMI 1640 medium containing 10% FCS, 200 units/ml penicillin, 200 mg/ml streptomycin. To prepare dilutions, suspensions were thawed from −70° C., diluted ten-fold with medium and then a two-fold dilution series was made. Control samples contained NC particle suspensions devoid of protein diluted identically. A second series of control samples contained a lysate of whole sporozoites (0.5 mg/ml of protein) prepared by freeze-thawing and sonicating sporozoites. Each sample was prepared in triplicate for each cell preparation with replicates placed randomly across plates. Plates were incubated for 96 hours at 41° C. in 5% $CO_2$, pulsed for the final 16 hours with 1mCi $^3$H-thymidine at 48 Ci/mmol (Amersham U.K.) then harvested (Dynatron Macromash Harvester, Dynatech Laboratories Ltd., Sussex, England) onto glass microfibre filters (MA781, Dynatron Laboratories Ltd.). After drying for 1h at 50° C. the discs were placed in scintillation vials, 3.5 ml of liquid scintillation cocktail (Scintillator 299™ Packard, Caversham, U.K.) was added and the radioactive incorporation measured in a scintillation spectrophotometer (Beckman Instruments Inc. LS9000).

2b. Results

Results are expressed as a stimulation index (SI) calculated for each sample with cells from each bird as follows:

$$SI = cpm1/cpm2$$

where:

cpm1=average counts per minute of triplicate cultures incubated with NC particles bearing protein.

cpm2=average counts per minute of triplicate cultures incubated with NC particles devoid of protein.

Solubilised NC strips containing polypeptides with relative molecular masses of approximately 49 kDa/45 kDa (collectively called 45 kDa) were found to stimulate the proliferation of lymphocytes from infected birds (see Table 1.). Lymphocytes from control birds were not stimulated to proliferate. The SIs varied from 4 to 9 and time-course studies showed that lymphocytes prepared from birds at 4 days after secondary infection proliferated most.

EXAMPLE 3

Raising and Screening of Antibodies to Lymphostimulatory Antigens 3.a. Methods 3.a.i. Immunisation of animals Pathogen-free rabbits (Harlan-Olac, Bicester, England) were maintained free of coccidia. Polypeptides of *E. maxima* H sporozoite pellets were solubilised, separated by SDS-polyacrylamide gel electrophoresis and transferred to NC as described in Example 1. NC strips bearing polypeptides with molecular masses of 45 kDa were excised, solubilised in DMSO as described in Example 1, washed in PBS pH 7.0 and finally suspended in 1 ml of PBS 7.0. Suspensions were injected subcutaneously into 4 sites (0.25 ml per site) and injections were repeated every 2 weeks using one NC strip per rabbit each time. Rabbit serum was prepared 2 weeks after the fourth injection.

Light Sussex chickens (3 weeks of age) were maintained free of coccidia. Polypeptides of *E. maxima* H sporozoite pellets were solubilised, separated by SDS-polyacrylamide gel electrophoresis and the gel stained briefly in an aqueous solution of Coomassie Brilliant Blue. A slice of polyacrylamide, containing polypeptides of molecular masses around 45 kDa was excised and chopped into small pieces. Gel pieces were decanted into a Schleicher & Schuell Biotrap chamber and the polypeptides electroeluted at 150V for 16 hours, according to the manufacturers instructions. Eluted protein was dialysed extensively against PBS pH 7.6 then treated with AG11A8 resin to remove any remaining traces of SDS. Antigen was mixed with Saponin (Sigma) and injected subcutaneously into the necks of the chickens (0.5 ml containing 5 ug Saponin and 1–5 ug protein per chicken) and injections repeated twice more at two weekly intervals. Chicken serum was prepared 2 weeks after the third injection.

3.a.ii. Screening of antisera by one and two-dimensional blotting

Polypeptides of *E. maxima* H sporozoite pellets were solubilised and separated by SDS-polyacrylamide gel electrophoresis as described in Example 1. Alternatively, sporozoites ($7 \times 10^7$) were suspended in 500 µl lysis buffer (0.2% Nonidet-P40, 2 mM CHAPS, 9M urea, 0.2% Biolytes 3–10 (Biorad), 1 mM DTT), sonicated (three ten-second bursts at 10 microns, MSE soniprep 50) and subjected to three cycles of freeze-thawing. Samples were centrifuged at 12,000 g in a microfuge for 1 minute then polypeptides separated by two-dimensional gel electrophoresis essentially as described by O'Farrell (J. Biol. Chem., 1975, 250: 4007–4021).

Separated polypeptides were transferred to NC paper as described in Example 1. The NC paper was immersed in TTN buffer (10 mM Tris-HCl pH 7.4, 500 mM NaCl, 0.05% Tween-20) containing 3% Bovine serum albumin (BSA) and incubated at room temperature, with gentle rocking, for 2 hours. The paper was rinsed in water, cut into strips and each strip incubated for 3 hours in a sample of rabbit serum diluted 1:250 in TTN containing 1% BSA. Strips were washed three times in TTN containing 0.5% Tween-20 then incubated for 1 hour in goat anti-rabbit IgG conjugated to alkaline phosphatase (Promega), diluted 1:7500 in TTN containing 1% BSA. Strips were washed a further three times in TTN containing 0.5% Tween-20 and once in AP buffer (100 mM Tris pH 9.5, 100 mM NaCl, 10 mM $MgCl_2$). Binding of the phosphatase conjugate was detected by incubating strips in AP buffer containing 50 mg/ml nitroblue tetrazolium and 50 mg/ml bromochloroindolyl phosphate.

3.b. Results

Figure 1:
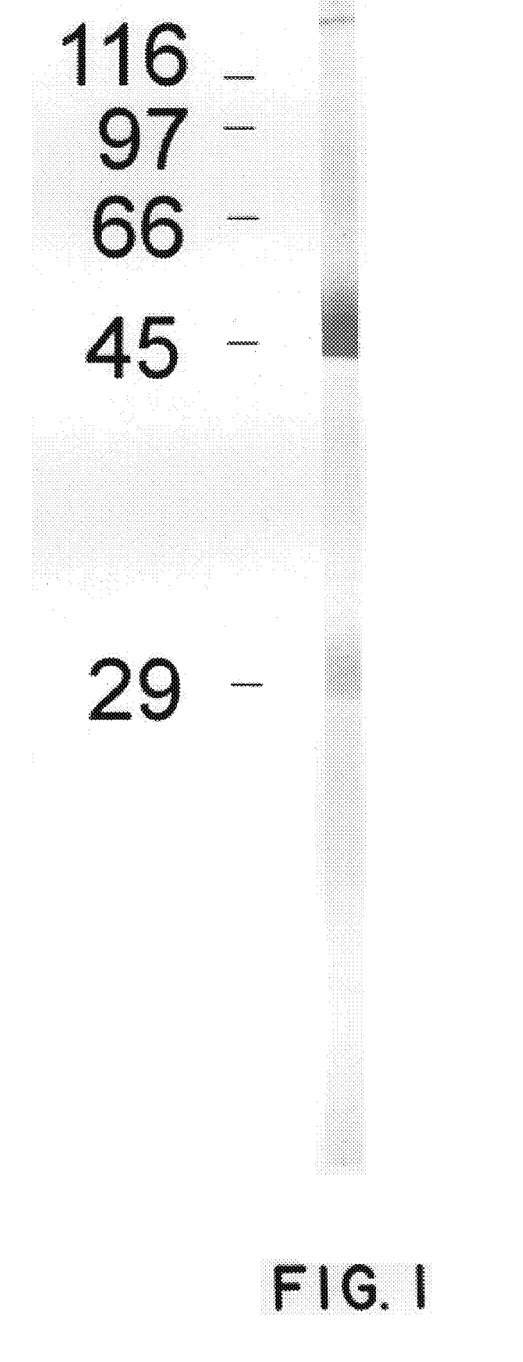
FIG. 1. Western blot of E. maxima sporozoite polypeptides probed with rabbit anti-p45 antibody.

The specificities of rabbit and chicken anti-p45 sera probed onto one-dimensional Western blots of polypeptides of *E. maxima* are shown in FIG. 1. Recognition of spots on two dimensional Western blots is summarised in Table 2.

EXAMPLE 4

Construction of an *E. maxima* Sporozoite cDNA Library 4.a. Methods 4.a.i. Isolation of mRNA

*E. maxima* sporozoites ($5 \times 10^8$) were purified as described in Example 1. Total cellular RNA was prepared using an RNA extraction kit (Pharmacia) according to the manufacturer's instructions. Briefly, sporozoites were lysed by incubation in buffered guanidinium thiocyanate, N-lauryl sarcosine and EDTA and RNA was separated from other cellular components by ultracentrifugation through buffered caesium trifluoroacetate. The RNA pellet was carefully dissolved in TE buffer (10 mM Tris-HCl pH 7.5, 1 mM EDTA) and stored at −70° C. as an ethanol precipitate. Messenger RNA was purified from this total RNA preparation using columns of oligo (dT) cellulose (poly(A) Quik, Stratagene) according to the manufacturer's instructions. Briefly, precipitated RNA was pelleted by centrifugation at 12,000 g for 30 minutes, air-dried and suspended in 400 µl of TE buffer containing 500 mM NaCl. The RNA was applied to the top of a column which was pre-equilibrated in the same buffer. Messenger RNA was eluted from the column with TE buffer that was pre-warmed to 65° C. and the amount of mRNA determined to be 2.6 µg by measuring the spectrophotometric absorbance at 260 nm. The mRNA was precipitated overnight at −70° C. by the addition of 0.1 volume 3M sodium acetate, pH 5.0, and 2.5 volumes absolute ethanol.

4.a.ii. Synthesis and cloning of cDNA cDNA was synthesised from messenger RNA using a ZAP-cDNA™ synthesis kit (Stratagene) according to the manufacturer's instructions. The cDNA population ranged in size from less than 200 bp to around 0 kbp as judged by agarose gel electrophoresis and autoradiography of a small portion of the synthesised cDNA. The remaining cDNA was end-repaired using T4 DNA polymerase in the presence of all four dNTPs at 37° C. for 30 minutes. EcoRI adaptors were ligated onto the blunted ends of the cDNA using T4 DNA ligase at 8° C. for 24 hours. Digestion with XhoI produced cDNA with XhoI restriction sites at all 3' ends and EcoRI restriction sites at all 5' ends. Oligonucleotides (excess adaptors and the restriction enzyme digested primer-template) were removed by centrifuging the sample through a 1 ml column of Sephacryl S-400.

100 ng portions of cDNA were ligated to 1 mg Uni-ZAP XR vector (Stratagene, digested with Eco RI and Xho I and dephosphorylated) overnight at 12° C. using T4 DNA ligase. Ligated DNA was packaged into phage heads using Gigapack II Gold packaging extract (Stratagene) according to the manufacturer's protocol. The resulting primary libraries were plated and amplified on *E. coli* SURE cells (Stratagene) and the resulting amplified libraries (Emx8 and Emx9) were titred on *E. coli* XL1-Blue cells (Stratagene) all according to manufacturer's instructions. Briefly, for all platings, host cells were grown overnight with shaking at 30° C. in L Broth supplemented with 0.2% (w/v) maltose and 10 mM MgSO$_4$. Cells were diluted to OD$_{600}$=0.5 with 10 mM MgSO$_4$ before use. The number of recombinants in each library was determined by plating phage in the presence of 0.4% (w/v) 5-bromo-4-chloro-3-indolyl-β-D-galactoside (Xgal) and 2.5 MM isopropylthio-β-D-galactoside (IPTG) (Northumbria Biologicals Ltd.).

4.b. Results

Emx8 contains 3×10$^8$ pfu/ml (65% recombinant) and Emx9 contains 6×10$^8$ pfu/ml (55% recombinant)

EXAMPLE 5

Identification of cDNA Clones Coding for *E. maxima* p45 Antigens.

5.a. Methods

Immunoscreening of cDNA libraries was done according to standard instructions supplied by Stratagene. The papers were immersed in rabbit anti-p45 serum diluted 1:100 in TTN containing 1% BSA. All further procedures were identical to those described for the development of Western blots in Example 3A. Positive plaques were identified and after storing overnight at +4° C. to elute bacteriophage particles, plaques were rescreened. Rescreening was continued until all the positives contained pure populations of antibody reactive plaques.

5.b. Results

Twenty two independent plaques (pEm45/1 to pEm45/22) which reacted with rabbit anti-p45 serum were isolated and plaque purified from libraries Emx8 and Emx9.

EXAMPLE 6

Analysis of cDNA Clones Coding for *E. maxima* p45 Antigens 6.a. Methods 6.a.i. Analysis of cDNA inserts Lambda phage particles were eluted from purified plaques that reacted with rabbit anti-p45 serum. cDNA inserts were rescued into plasmid pBluescript by in vivo excision from recombinant lambda ZAPII according to instructions supplied by the manufacturer (Stratagene). pBluescript plasmids containing cDNA were isolated by alkaline lysis (Birnboim and Doly, 1979, Nucleic Acids Res., 7: 1513) and cDNAs analysed by digestion with restriction endonucleases.

6.a.iii. DNA sequence determination pEm45/9 was purified by equilibrium centrifugation in CsCl/ethidium bromide gradients and the nucleotide sequence of the cDNA insert was determined directly from the double stranded DNA template using T3 and T7 oligonucleotide primers (Stratagene) and Sequenase version 2.0 (United States Biochemical) using instructions supplied by the manufacturers.

6.b. Results

The nucleotide sequence of pEM45/9 and it's deduced amino acid sequence is shown in SEQ. ID. NOS.1 and 2. pEm45/9 is a 392 bp cDNA including a 3' polyA sequence. The cDNA appears to be "open" from the third nucleotide to an opal termination codon (TGA) at 329 bp which precedes the poly(A) sequence. The deduced amino acid sequence encodes a protein of 109 amino acids or approximately 12 kilodaltons. The cDNA has unique Bsm I (213 bp), Hind III (260 bp) and Sph I (323 bp) restriction enzyme sites.

EXAMPLE 7

Expression of the Recombinant Protein Encoded by pEM45/9.

7.a Methods 7.a.i. Construction of plasmid pGEX3XEM45/9

1 µl of pEM45/9 was digested with 10 units of Bam HI and 10 units of Xho I for 2 hours at 37° C. and the released cDNA insert ligated into Bam HI-Xho I digested, dephosphorylated plasmid pRSETB (InVitrogen). Ligated DNA was transfected into *E. coli* strain JM109, colonies containing recombinant plasmid pRSETBEM45/9 were identified and plasmid DNA was isolated by alkaline lysis (Birnboim and Doly, 1979, Nucleic Acids Res., 7: 1513).

1 µl of pRSETBEM45/9 was digested with 10 units of Eco RI and the released cDNA insert ligated into Eco RI digested, dephosphorylated plasmid pGEX3X (Pharmacia). Ligated DNA was transfected into *E. coli* strain JM101, bacteria harbouring recombinant plasmids were selected and plasmid DNA was isolated as above. DNAs were analysed by restriction enzyme digestion and agarose gel electrophoresis to identify a plasmid, pGEX3XEM45/9 which contained the cDNA insert of pEM45/9 in the correct orientation for protein expression as a fusion with glutathione S-transferase.

7.a.ii Expression of Glutathione S-Transferase(GST)-EM45/9 fusion protein

Bacterial colonies were picked into L-broth containing 100 µg/ml Ampicillin and grown overnight at 37° C. with vigorous shaking. 50 µg of overnight culture were used to seed 5 ml of fresh medium and cultures were re-incubated until the absorbance (measured at 600 nm) was approximately 0.3. IPTG was added to a final concentration of 1 mM and the cultures continued for a further 4 to 5 hours. Aliquots of bacterial cultures were removed at various times throughout the incubation and examined by PAGE and Western blotting with antibodies raised to native p45 antigen as described in Example 3.a.ii.

2 ml of an overnight culture were used to seed 200 ml of fresh medium and the culture grown as above. Five hours after the addition of IPTG to 1 mM, the bacterial cells were harvested by centrifugation and resuspended in 5 ml of PBS containing 1% v/v Triton-X-100. Cells were sonicated for four 30 second bursts on full power (MSE, Soniprep) and the sonicate separated into supernatant and pellet by centrifugation. The pellet was solubilised in either 8M urea or 2% SDS prior to examination by PAGE and Western blotting.

7.b. Results

Figure 2:
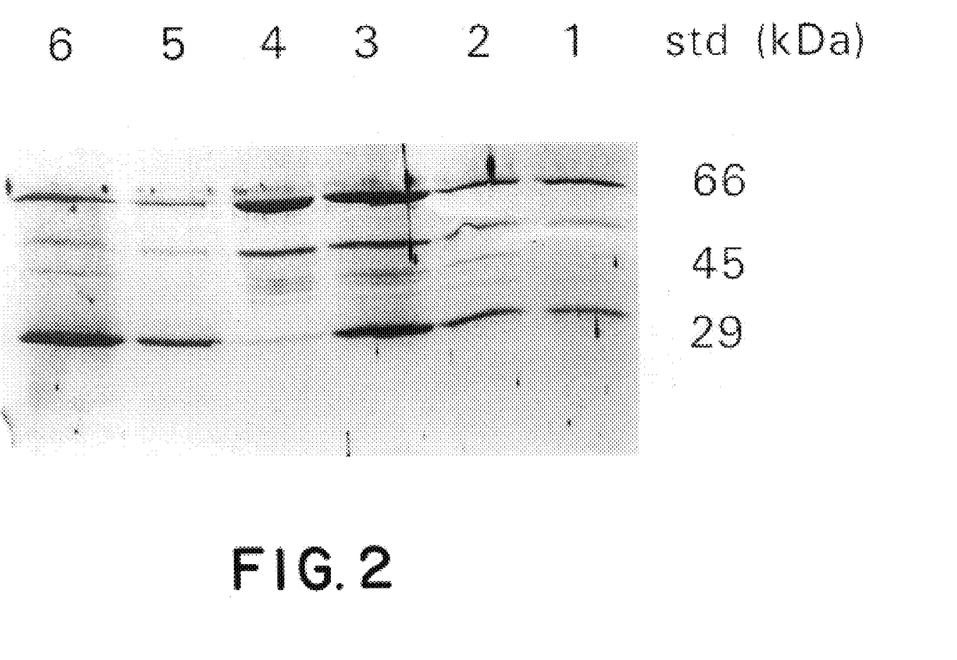
FIG. 2. Western blot of pGEx3xEM45/9 expression. Lanes: std =molecular weight markers (in kDa), 1=overnight culture of pGEx3xEm45/9, 2=culture grown to absorbance (600 nm) of 0.3 (IPTG was added to a concentration of 1 mM at this time point), 3=culture 3.5 hours after addition of IPTG, 4=soluble lysate after sonication and centrifugation of the IPTG induced culture, 5=pellet after sonication and centrifugation that was soluble in 8M urea, 6=pellet after sonication and centrifugation that was only soluble in 2% SDS.

Recombinant GST-EM45/9 protein was successfully expressed in E. coli as judged by the screening of Western blotted bacterial lysates with either rabbit or chicken anti-p45 antisera. The fusion protein which specifically reacted with the sera was of approximately 37 kDa which is accounted for by 26 kDa being GST and 11 kDa being EM45/9 (FIG. 2, lane 1.) The protein was produced in the overnight culture but expression was significantly increased by the addition of IPTG (FIG. 2, lane 3). Following sonication of a harvested culture, very little recombinant protein was detected in the supernatant (FIG. 2, lane 4), whereas a high concentration was found in the pellet and was solubilised in 2% SDS (FIG. 2, lane 6). The pellet was partially soluble in 8M urea (FIG. 2, lane 5).

EXAMPLE 8
Preparative Electrophoresis of pGEX3XEM45/9 Fusion Protein 8.a Methods Two aliquots of 1 ml of SDS-solubilised fustion protein, prepared as described in Example 7.a.ii. were electrophoresed as described in Example 1A.ii. After electrophoresis, 1 cm vertical slices were cut from each side of the gel and stained for 10 min in 0.125% Coomassie Brilliant Blue in 45% v/v methanol, 10% v/v acetic acid. The remainder of each gel was incubated in 45% v/v methanol, 10% v/v acetic acid. Stained slices were briefly destained then the whole gels reassembled on a glass tray over a light box. The regions containing recombinant pGEX3XEM45/9 protein were excised from the central, unstained, sections of the gels and were finely chopped. Gel pieces were decanted into a dialysis bag in a small volume of buffer containing 25 mM Tris pH 8.3, 192 mM glycine, 0.1% SDS. The sealed bag was placed in an agarose electrophoresis chamber filled with the same buffer and the fusion protein electro-eluted at 50v for 16 hours. Buffer containing fusion protein was removed from the bag, dialysed extensively against PBS, pH 7.6 then treated with AG11A8 resin according to instructions from the manufacturer (Biorad) to remove any remaining traces of SDS. Samples of this antigen were analysed by SDS-PAGE and Western blotting.

8.b. Results

Figure 3:
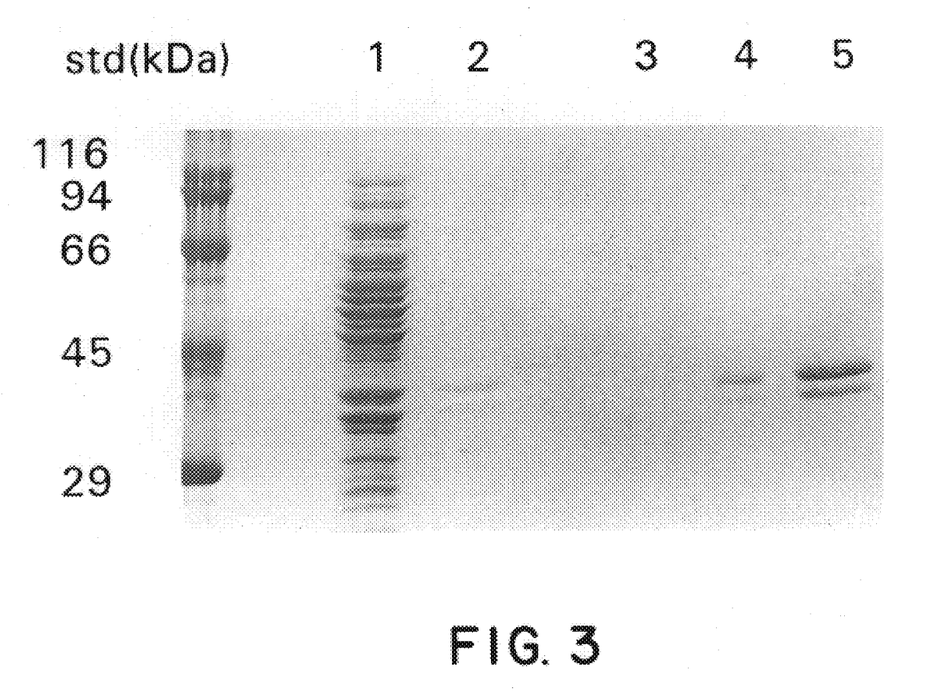
FIG. 3. SDS-PAGE of electroeluted pGEX3XEm45/9 fusion protein. Lanes: std=molecular weight markers (in kDa), 1=culture of pGEX3XEm45/9 4.5 hours after addition of IPTG, 2=electroeluted fusion protein, 3=1 μl concentrated (Centrion contracter, Amicon) electroeluted fusion protein, 4=5 μl of [3], 5=20 μl of [3]. Horizontal arrow shows protein recognized by the chicken anti-p45 serum in FIG. 4.
Figure 4:
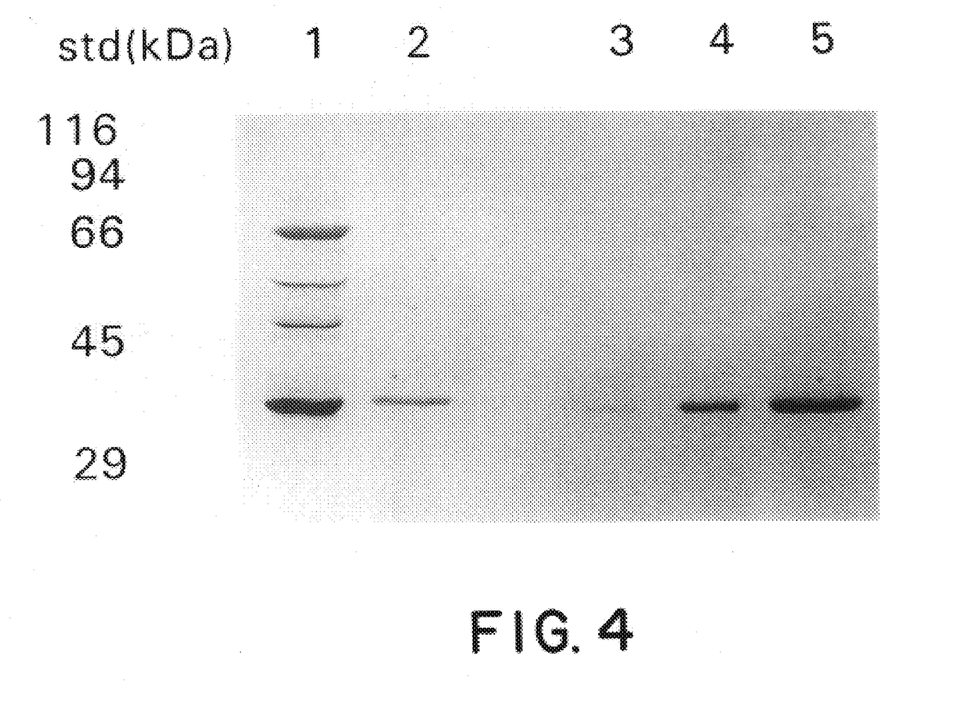
FIG. 4. Western blot of electroeluted pGEX3XEm45/9 fusion protein probed with chicken anti-p45 serum. Lanes: std =molecular weight markers (in kDa), 2=culture of pGEX3XEm45/9 4.5 hours after the addition of IPTG, 3=electroeluted fusion protein, 3=1 μl concentrated electroeluted fusion protein, 4=5 μl of [3], 5=20 μl of [3].

Approximately 200 μg of protein was electroeluted from two acrylamide gel slices. The content of this antigen was analysed by SDS-PAGE (FIG. 3) and by probing a Western blot with anti-p45 serum (FIG. 4). For both figures, lane 1 contains a sample of the bacterial culture after four to five hours induction with IPTG and lane 2 contains a sample of the electroeluted antigen used for an immunisation experiment (Example 9) and for testing in an in vitro lymphoproliferation assay (Example 10).

EXAMPLE 9
Immunisation of Chickens with Fusion Protein pGEX3xEM45/9 Confers Protection Against Challenge Infection with Eimeria maxima.

9.a. Methods 9.a.i Immunisation of animals

Thirty six Light Sussex birds were reared under coccidia-free conditions until three weeks of age. Birds were randomly assigned to two groups and were housed individually in single bird cages. Samples of blood were taken and eighteen birds were immunised by subcutaneous injection (0.1 ml) of 10 ug antigen (prepared as described in Example 8) and 5 ug of Saponin in PBS. The remaining eighteen birds were mock-immunised by subcutaneous injection (0.1 ml) of 5 ug Saponin in PBS. Immunisations were repeated twice more at two weekly intervals and blood samples were taken following each immunisation.

9.a.ii. Challenge of animals

Two weeks after the final immunisation, all birds were given 100 sporulated oocysts of E. maxima by oral intubation. The faeces of each bird were harvested, by daily collections onto papered trays and the total number of oocysts excreted by each bird from 5 to 10 days post-challenge was calculated by counting mixed and diluted samples of faeces in Macmaster counting chambers.

9.b Results

Table 3 shows the individual oocyst outputs and group means of the two groups of birds either immunised with antigen or mock-immunised. Birds which received antigen had oocyst outputs 44% lower than the mock-immunised group indicating that the antigen, as described in Example 8, can be used to protect chickens against infection with Eimeria maxima.

EXAMPLE 10
Recombinant Protein pGEX3XEM45/9 is Lymphostimulatory 10.a. Methods

Peripheral blood lymphocytes were prepared from blood samples taken after the third immunisation in Example 9. The method of preparation was identical to that described in Example 2.a.ii. To each well, 100 μl of the antigen prepared in Example 8, diluted in PBS to a concentration of 0.2 ug/ml, was added and the lymphostimulation assay continued as described in Example 2.a.ii.

10.b. Results

Figure 5:
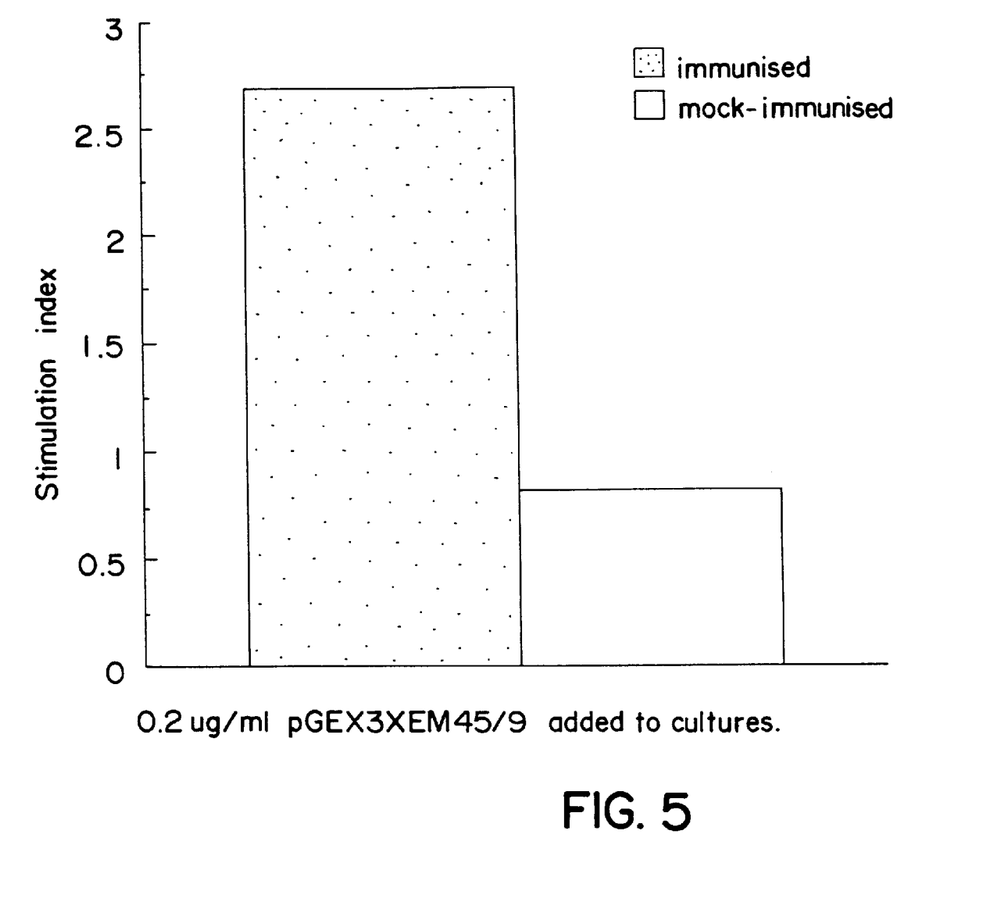
FIG. 5. Mean stimulation index for cells from birds immunised with antigen compared to birds mock-immunised.

FIG. 5. shows the mean stimulation index for cells from birds immunised with the antigen compared to the mean stimulation index for cells from birds mock-immunised. The immunised birds were stimulated four-fold above the mock-immunised birds indicating that the recombinant antigen pGEX3XEM45/9 had a specific lymphostimulatory effect on the cells.

Legend to the figures.

TABLE 1

Stimulation Indices of Immune and Control birds exposed to nitrocellulose-bourne antigens of E. Maxima sporozoites. Each S.I. is the mean of ten individual birds.

| Strip number (Mr) | Experiment 1 Immune birds | Experiment 2 Immune birds | Experiment 1 Control birds | Experiment 2 Control birds |
|---|---|---|---|---|
| 11 (49 kD) | 5.04 | 4.51 | 1.12 | 1.41 |
| 12 (45 kD) | 2.48 | 5.12 | 1.32 | 1.63 |

TABLE 2

2-D gel analysis of E. maxima H sporozoites - identification of spots which are recognised by anti-45 kDa serum and are lymphostimulatory.

| Spot no. | Recognised by anti-p45 serum | lymphostimulatory |
|---|---|---|
| 11 | + | − |
| 12 | + | − |
| 17 | + | + |
| 18 | + | − |
| 25 | + | + |
| 26 | + | + |
| 27 | + | − |
| 28 | + | − |
| 29 | + | − |
| 34 | + | − |
| 43 | + | − |
| 54 | + | − |

TABLE 3

In vivo protection against challenge infection with E. maxima: Oocyst outputs of birds immunised with fusion protein pGEX3XEM45/9 compared to mock-immunised controls.

| Group | Bird No | Oocytst output ($\times 10^6$) | mean | SD |
|---|---|---|---|---|
| Immunised | 1 | 34.2 | 18.7 | 11.5 |
| | 2 | 46.8 | | |
| | 3 | 13.6 | | |
| | 4 | 37.6 | | |
| | 5 | 11.7 | | |
| | 6 | 26.6 | | |
| | 7 | 15.4 | | |
| | 8 | 7.3 | | |
| | 9 | 8.7 | | |
| | 11 | 10.3 | | |
| | 12 | 9.5 | | |
| | 13 | 10.6 | | |
| | 14 | 16.0 | | |
| | 15 | 12.9 | | |
| | 16 | 24.8 | | |
| | 17 | 11.8 | | |
| | 18 | 20.5 | | |
| Mock-Immunised | 19 | 41.9 | 33.5 | 15.1 |
| | 20 | 49.1 | | |
| | 21 | 27.1 | | |
| | 23 | 31.2 | | |
| | 24 | 38.1 | | |
| | 25 | 11.4 | | |
| | 26 | 22.1 | | |
| | 27 | 48.5 | | |
| | 28 | 39.3 | | |
| | 29 | 23.3 | | |
| | 30 | 44.4 | | |
| | 31 | 40.5 | | |
| | 32 | 23.0 | | |
| | 33 | 8.5 | | |
| | 34 | 21.0 | | |
| | 35 | 31.3 | | |
| | 36 | 68.2 | | |

We claim:

1. An Eimeria T-lymphocyte stimulatory protein, comprising the amino acid sequence shown in SEQ ID NO:2.

2. A vaccine for the protection of poultry against coccidiosis comprising a protein according to claim 1 together with a pharmaceutically acceptable carrier.

3. A process for the preparation of a coccidiosis vaccine, comprising formulating a protein according to claim 1 into a veterinarial preparation with immunizing activity.

4. An immunochemical reagent comprising a protein according to claim 1, said reagent being bound to a support or provided with a labelling substance.

5. A method for the protection of poultry against coccidiosis, comprising administering a vaccine according to claim 2 to the poultry.

6. A process for the preparation or a coccidiosis vaccine, comprising formulating a protein obtained by culturing a host cell transformed with a nucleic acid sequence encoding a protein according to claim 1 into a veternarial preparation with immunizing activity.

* * * * *

UNITED STATES PATENT AND TRADEMARK OFFICE
CERTIFICATE OF CORRECTION

PATENT NO. : 6,001,363
DATED : December 14, 1999
INVENTOR(S) : F.M. Tomley et al.

It is certified that error appears in the above-identified patent and that said Letters Patent is hereby corrected as shown below:

Claim 6, line 1, change "or" to -- of --.

Signed and Sealed this

Eighteenth Day of July, 2000

Attest:

Q. TODD DICKINSON

Attesting Officer

Director of Patents and Trademarks